United States Patent
Haney

[11] Patent Number: 5,891,914
[45] Date of Patent: Apr. 6, 1999

[54] BIOACTIVE TOPICAL SILOXANE COMPOSITIONS HAVING ENHANCED PERFORMANCE AND SAFETY

[75] Inventor: David N. Haney, San Diego, Calif.

[73] Assignee: Special Advanced Biomaterials, Inc., Ogdensburg, Wis.

[21] Appl. No.: 487,027

[22] Filed: Jun. 7, 1995

Related U.S. Application Data

[62] Division of Ser. No. 675,749, Mar. 27, 1991, Pat. No. 5,686,065.

[51] Int. Cl.$^6$ .................................................. A61K 31/695
[52] U.S. Cl. ...................... 514/569; 424/405; 424/401; 424/59; 424/60; 424/76.1; 424/63; 424/65; 424/78.03; 424/78.06; 424/DIG. 10; 514/919
[58] Field of Search ................................ 424/59, 60, 405, 424/401, 76.1, 63, 65, 78.03, 78.06, DIG. 10; 514/569, 919

[56] References Cited

U.S. PATENT DOCUMENTS

| | | |
|---|---|---|
| 2,681,878 | 6/1954 | Kauppi . |
| 2,698,824 | 1/1955 | Morgulis . |
| 2,929,829 | 3/1960 | Morehouse . |
| 2,950,986 | 8/1960 | Bailey et al. . |
| 2,973,383 | 2/1961 | Black . |
| 3,068,152 | 12/1962 | Black . |
| 3,068,153 | 12/1962 | Morehouse . |
| 3,392,040 | 7/1968 | Kass . |
| 4,172,122 | 10/1979 | Kubik et al. . |
| 4,172,904 | 10/1979 | Young et al. . |
| 4,200,664 | 4/1980 | Young et al. . |
| 4,311,695 | 1/1982 | Starch . |
| 4,423,041 | 12/1983 | Clum et al. . |
| 4,500,337 | 2/1985 | Young et al. . |
| 4,500,338 | 2/1985 | Young et al. . |
| 4,500,339 | 2/1985 | Young et al. . |
| 4,552,755 | 11/1985 | Randen . |
| 5,160,494 | 11/1992 | Krzysik et al. . |
| 5,247,111 | 9/1993 | Oolenick . |

FOREIGN PATENT DOCUMENTS

| | | |
|---|---|---|
| 309969 | 10/1992 | European Pat. Off. . |
| 4149233 | 5/1992 | Japan . |
| 5132556 | 5/1993 | Japan . |
| 5139949 | 6/1993 | Japan . |
| 8903851 | 5/1989 | WIPO . |

OTHER PUBLICATIONS

Chemistry and Technology of Silicones, W. Noll, Chapter 10, Academic Press, 1968 E.P. Plueddmann, Silane Coupling Agents, Plenum Press, 1982.
D.E. Leyden and W. Collins, Silylated Surfaces, Gordon and Breach, 1980, pp. 189, 201, 363.

*Primary Examiner*—Raj Bawa
*Attorney, Agent, or Firm*—Philip G. Meyers

[57] ABSTRACT

Methods and compositions that provide for the long-term adhesion and slow-release of various bioactive agents on the surface of human skin utilize siloxane bridging agents activated for reaction with the skin surface which bind the bioactive agent to the skin surface. Since the topical agent remains bound to the continuously renewing epidermis, safety is enhanced for many bioactive agents. Slight modifications of the siloxane bridging compounds or bioactive agents allows for more or less adhesion to the skin, controlling the degree of release of the agent. Skin treatments according to the invention can provide enhanced repellency to microorganisms, insect bites, sun, water, poison ivy/oak, and other skin irritants, and other effects such as artificial skin coloring and administration of topical drugs, among others.

22 Claims, 1 Drawing Sheet

BIOACTIVE TOPICAL SILOXANE COMPOSITIONS HAVING ENHANCED PERFORMANCE AND SAFETY

This is a divisional of U.S. Ser. No. 07/675,749 now U.S. Pat. No. 5,686,065 issued on Nov. 11, 1997, filed on Mar. 27, 1991, entitled BIOACTIVE TOPICAL SILOXANE COMPOSITIONS HAVING ENHANCED.

FIELD OF THE INVENTION

This invention relates to methods and compositions for the long-term adhesion and/or slow-release of bioactive agents on human and animal skin surfaces. In particular, this invention relates to the preparation and use of siloxane compounds that perform as a topical agent delivery system, bridging the skin surface and bioactive agent.

BACKGROUND OF THE INVENTION

Many bioactive topical agents, such as sunscreens, moisturizers, repellents, antimicrobials, and other pharmaceuticals, are intended for use on the surface of human skin. Such agents are generally effective only as long as the agent persists on the skin. As a result, however, of normal daily activities, for example, perspiring, washing, or wearing clothes, a topical agent loses its activity due to premature removal. Despite recognition of this substantivity problem, i.e., the problem of significantly sustained presence of the topical agent, no satisfactory solution has been proposed in the prior art.

Attempts to prolong substantivity of a topical agent have focused on developing compositions which incorporate excessive amounts of water-insoluble materials. These formulations result in cosmetically undesirable surface coatings and occlusion of the skin, yet do not substantially enhance the substantivity of the bioactive agent. Many commercially available topical formulations consist of an oily carrier of base such as mineral oil or a fatty acid ester, or a polymeric carrier or base such as polymethacrylate or polydimethylsiloxane which is insoluble or nearly insoluble in water, plus a bioactive agent (e.g., an ultraviolet-absorbing or antimicrobial agent). Such compositions tend to be greasy, tacky, occlusive (cause excess perspiration), and also tend to stain clothing. These water-insoluble compositions only provide minimal wash-resistance and do little to control the release of the bioactive agent either off of the skin or into the blood. Alternative attempts to prolong substantivity of topically delivered bioactive agents have focused on developing band aid-like patches. This approach is cosmetically undesirable.

There has been considerable interest in the use of organopolysiloxane compounds as surface agents. Organopolysiloxanes exhibit a broad spectrum of properties depending on molecule size, side-chain group type, and the degree of cross-linking between chains. These polymers, which are predominantly polymethylsiloxanes and polymethylphenylsiloxanes, are generally safer and more resistant to attack by temperature, sun, water, ozone, chemicals, corona discharge, dirt, and shear than their carbon counterparts. As a result, many of these polymers have been used as surface protective agents for inanimate substrates. For example, silicones have been used as insulators in high temperature electric machines, as lubricants for high stress, shear, and temperature environments, and as weather protection and water repellency treatments for masonry, leather, textile, paper, metal, and glass surfaces. See, for example, W. Noll, *Chemistry and Technology of Silicones*, Chapter 10, Academic Press, 1968.

Fully polymerized siloxane compounds have also been used in the formulation of cosmetics, pharmaceuticals, and artificial implants. General inertness, high performance under stress, and specific ability to retard blood clotting are key qualities of silicone biological implants. In cosmetic and pharmaceutical formulations for skin applications, polysiloxanes are typically used as the carrier (or part of the carrier) to provide a non-greasy, low vapor pressure, inert matrix for the bioactive ingredient. Polysiloxanes have been used, for example, (1) to provide a water-insoluble, low vapor-pressure matrix for insect repellents as described in Kauppi U.S. Pat. No. 2,681,878, issued Jun. 22, 1954 and for skin protectants as described in Morgulis U.S. Pat. No. 2,698,824, issued Jan. 4, 1955; (2) to provide a non-greasy cosmetic formulation as described in Kass U.S. Pat. No. 3,392,040 issued Jul. 9, 1968; (3) to provide a non-tacky cosmetic formulation as described in Clum et al. U.S. Pat. No. 4,423,041 issued Dec. 27, 1983; and (4) to provide a non-irritating matrix for topical agents as described in Starch U.S. Pat. No. 4,311,695, issued Jan. 19, 1982. These preparations involve polymerization of the siloxane compounds prior to skin contact.

Other silicon-based compounds known as silane coupling agents are used as adhesives for bridging dissimilar materials. Methods for preparing silane coupling agents, also called polymerizable silanes and hydrolyzable silanes, and use of such compounds to provide adhesion between dissimilar inanimate materials such as glasses, metals, textiles, and composite polymers, is well known. See, for example, E. P. Plueddmann, *Silane Coupling Agents*, Plenum Press, 1982.

The use of silane coupling agents with biomaterials is more recent. Enzymes and proteins have been immobilized on silanized glass. See for example, D. E. Leyden and W. Collins, *Silylated Surfaces*, Gordon and Breach, 1980, pp. 189, 201, 363. The technique typically involves silylation of porous glass using $\gamma$-aminopropyltriethoxysilane, i.e., modification of the glass surface with a polymerizable silane, followed by enzyme/protein reaction with the amine of the aminopropyl glass. This provides a means to effect analytical separation and purification of antibodies and enzymes.

Silane coupling agents have also been used along with other polymers to create cross-linked polymer meshes and cages which typically entrap a biogenic agent such as an insecticide or microbiocide. See, for example, Young et al. U.S. Pat. Nos. 4,172,904 issued Oct. 30, 1979; 4,200,664, issued Apr. 29, 1980; 4,500,337, issued Feb. 19, 1985; 4,500,338, issued Feb. 19, 1985; and 4,500,339, issued Feb. 19, 1985. Such physical entrapment using acrylic polymers for skin topicals has also been described. See, for example, Kubik et al. U.S. Pat. No. 4,172,122 issued Oct. 23, 1979 (sunscreens), and Randen U.S. Pat. No. 4,552,755, issued Nov. 12, 1985 (moisturizing compositions).

Sunscreen formulations have been prepared using silane coupling agents which are polymerized prior to skin contact. See, for example, Morehouse U.S. Pat. Nos. 2,929,829, issued Mar. 22, 1960 and 3,068,153, issued Dec. 11, 1962; Bailey et al. U.S. Pat. No. 2,950,986, issued Aug. 30, 1960; and Black U.S. Pat. Nos. 2,973,383, issued Feb. 28, 1961 and 3,068,152, issued Dec. 11, 1962. Typically, these compositions involve the preparation of a silane coupling agent modified with a sunscreen, followed by formulation into a water-containing base. Specific examples include the preparation of two p-aminobenzoic acid (PABA) derivatives (one via amide derivatization of the PABA-amine and one via amide derivatization of the PABA-carboxyl) and one benzophenone derivative (a sulfonic acid salt) that carry the triethoxysiloxane group (a polymerizable oxysilane). These materials are then formulated into an aqueous solution or creme for end use. The method of formulation incorporates substantial amounts of water (and in most cases, heat as well) which causes polymerization of the silane coupling agent prior to use on the skin.

Ideally, a topical agent should possess several characteristics in order for the bioactive agent to work effectively, efficiently, and safely. It should be non-toxic and without side effects, non-irritating, non-greasy, tackless, odorless, invisible, non-staining, easy to apply, and not easily removed by normal activities so it will provide full bioactive functionality for extended time periods (i.e., 1–7 days). The present invention provides topical agents which have these characteristics to a greater extent than many prior preparations.

SUMMARY OF THE INVENTION

This invention provides siloxane and polysiloxane compositions bound to the skin from formulations of a silane coupling agent and a bioactive agent. A topical composition according to the invention comprises (1) a silane coupling agent and one or more bioactive agents, and/or (2) a bifunctional compound which combines both silane coupling and bioactive groups. Polymerization of either of these compositions occurs upon contact with the skin surface, allowing both the skin and the bioactive agent(s) to become cross-linked into the polysiloxane polymer.

The invention also concerns methods for preparing the bifunctional compositions and silane coupling agent/bioactive agent formulations. The latter are stable until end use, then react to form the siloxane or polysiloxane rapidly upon delivery to the skin.

This invention also provides methods for delivering a chemically reactive bridging silane compound to the skin surface at the time of end use. This skin surface retention methodology utilizes silane bridging agents that are activated to silanols for reaction with the skin surface groups as well as bioactive agent groups at the time of end use. According to one method, a silane coupling agent substituted with a bioactive agent is formulated and stored in an anhydrous vehicle, then applied directly to the skin. Moisture on the skin surface or water added at the time of delivery causes the silane to simultaneously polymerize and bond to the skin surface molecules. In another method, a silane coupling compound and the bioactive agent are formulated and stored separately, and both are applied to the skin, either simultaneously or one after another, to form the topical siloxane or polysiloxane bound to both the skin and the bioactive agent. Various novel compounds and compositions used in these methods also form part of the invention, as described in detail hereafter.

BRIEF DESCRIPTION OF THE DRAWINGS

In the accompanying drawing.

DETAILED DESCRIPTION

The present invention describes silanes, bioactive agents, and formulations of such compounds to obtain siloxane and polysiloxane materials which substantially increase the adhesion to skin, the wash- and wear-resistance from skin, and the option to provide slow release from skin for bioactive agents. By utilizing a bridging material such as a silane that rapidly hydrolyses into a silanol, the invention can enhance the substantivity of a variety of topical bioactive agents, and diminish oiliness, greasiness, tackiness, and occlusion by decreasing the amount of material that needs to be applied.

The term "silane coupling agent(s)", for the purposes of the present invention, means any silane monomer or oligomer which, when exposed to water, forms a silanol or a polysiloxanol that can react with (1) itself, e.g., to form a polysiloxane polymer, (2) with active groups (like alcohols, amines, etc.) on the skin, and (3) bioactive agents, thereby incorporating these groups into the siloxane or polysiloxane. The term "bioactive agent" (or "skin surface functional agent") refers to a compound which protects or otherwise benefits the skin of a human or animal when applied topically as a substituent of the above-described siloxane or polysiloxane. Such skin surface functional agents include sunscreens, antimicrobials, deodorants, skin protectants, chemical repellents, skin moisturizers, insect repellents, skin colorants, topical pharmaceuticals, and the like. The term "skin" for purposes of the invention refers to all human or animal external surfaces including the epidermis, mucous membranes, cornea, nails, teeth, and hair. While many applications will be limited to the epidermis, nails and hair for toxicological reasons, applications for the other surfaces are contemplated.

A key requirement of the invention is that the topical compositions react upon contact with the skin and thereby bind to the skin more securely than prepolymerized siloxanes, thus overcoming the defects of prior art compositions for skin substantivity. Since this chemistry results in maintaining the topical agent bound to the continuously renewing epidermis, substantially enhanced safety can be obtained for many agents due to diminished skin penetration. Modification of the silane bridging agent can produce a bond between the silicon atoms and the groups on the bioactive agent or skin having a greater or lesser tendency to hydrolyze. This allows more or less adhesion to the skin and can provide either essentially semipermanent adhesion or timed release of the bioactive agent, as discussed below.

The bridging concept involves a ternary molecular complex which can be represented as:

Skin---Siloxane---Bioactive Agent

Figure 1:
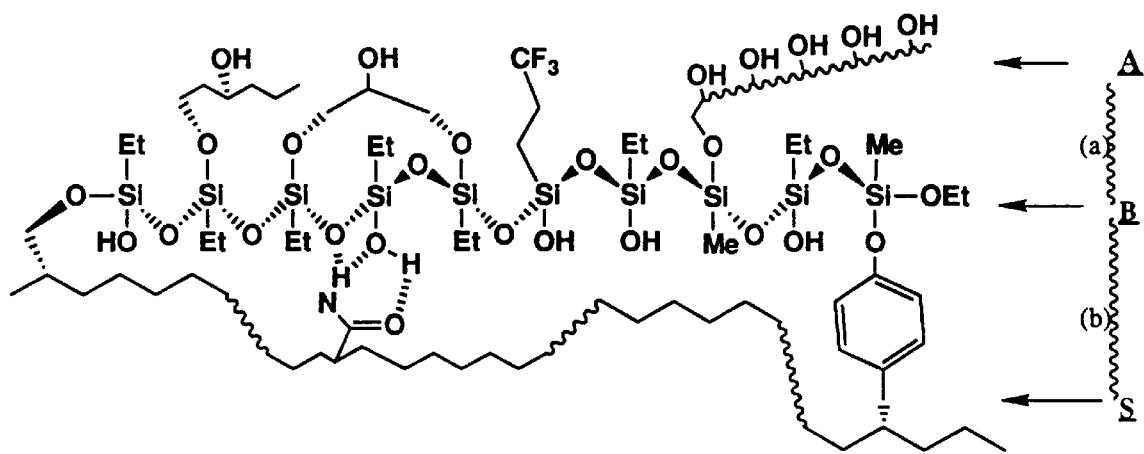
FIGS. 1 and 2 are schematic structural diagrams of two representative topical siloxane compounds according to the invention bound to the skin.

FIG. 1 provides a more detailed representation of such a complex. A preferred form of the molecular complex represented above has the formula:

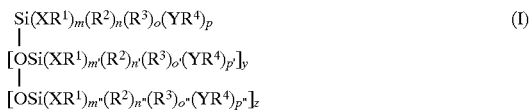

wherein —$XR^1$ represents the bioactive agent attached to the silicon atom; $R^2$ represents a group that adjusts toxicity and aesthetic/cosmetic properties such as viscosity, feel and the like; $R^3$ is a skin surface group; $R^4$ represents unreacted coupling groups of the type which react to form a siloxane polymer or oligomer, react with the skin, or react with bioactive compounds of the formula IIIB as described below; X is a linking group wherein an N, C, O, S or P atom is directly bonded to the Si atom, such as —NR—, —$CR_2$—, —O—, —S—, or —P—, wherein R is hydrogen or a substituted or unsubstituted hydrocarbyl group, generally a lower (e.g., $C_1$–$C_4$) substituted or unsubstituted alkyl group, forming a linkage $R^1$—X—Si; Y is a linking group wherein an N, O, S or P atom is directly bonded to the Si atom, such as —NH—, —NR—, —CH$_2$—, —CHR—, —CR$_2$—, —O—, —S—, —PH—, —PR—, —O—CO—, —NH—CO—O—, —NR—CO—, or —NH—CO—NH—, Y being most preferably an oxygen atom (—O—); y is from 0 to about 1 million, preferably 0 to 100,000; z is 0 or 1, provided that if z=0 then y=0; m, n, o, p, m', n', o', p', m", n", o" and p", which may each be the same or different, are each 0, 1, 2, 3 or 4, provided that the sum of m+n+o+p is from 3 to 5, preferably 3 or 4, the sum of m'+n'+o'+p' for each Si atom is from 2 to 3, preferably 2, and the sum m"+n"+o"+p" is from 3 to 4, preferably 3, and further provided that:

(1) the molecule contains at least one group —XR$^1$ and at least one group R$^3$;

(2) the molecule contains at least one group R$^3$ for approximately each 1,000 silicon atoms, preferably for each 100 silicon atoms; and (3) the molecule contains at least one group —XR$^1$ for approximately each 200 silicon atoms, preferably for each 20 silicon atoms.

Silicon usually has a valency of 4, but can have a valency of 5, hence the possibility that m+n+o+p=5. Where y+z is in the range of about 1–5,000, the resulting compound is an oligomer; where y+z is 5,000–1,000,000, the resulting compound is a polymer.

In the above formula (I), representative groups for R$^1$ vary widely and are described below. R$^2$ is preferably C$_1$–C$_{20}$ substituted (e.g., with halogen as in —CF$_3$) or unsubstituted alkyl, aryl or aralkyl group. R$^3$ is preferably a group on the skin surface terminating in an N, O or S atom which is bonded directly to the Si atom, such as a protein acyl group (as in aspartic or glutamic acid or the C-terminal group), a protein amine, guanidine, or imidazole group (as in lysine, histidine, arginine, or the N-terminal) a protein amide group (as in the backbone or asparagine or glutamine), a protein sulfur group (as in cysteine, methionine, or cystine) or a tightly protein-bound water molecule. R$^4$ is preferably H or C$_1$–C$_{20}$ substituted or unsubstituted alkyl, aryl or aralkyl group, or a monovalent metal M such as sodium or potassium, suitable for forming a non-toxic byproduct upon reaction. R$^4$=CH$_3$ and Y=O, for example, is not preferred because the resulting byproduct upon hydrolysis is methanol. Even if Y is other than oxygen, the siloxane polymerization reaction which occurs spontaneously in the presence of water results in a siloxane (—Si—O—Si—O—Si—) chain.

It is possible or even likely that siloxane polymers or oligomers according to formula (I) wherein the sum of y+z>0 will not have a skin attachment site for every silicon atom. However, as noted above, the reaction should yield at least one attachment point for every 1000 silicon atoms, preferably every 100 silicon atoms, to provide sufficient adhesion. Similarly, it is possible that skin or bioactive agent functionality is not attached to every silicon, but present sporadically along a polysiloxane chain as represented in FIG. 1. The group R$^4$, which may be left over from the siloxane-forming reaction, is not needed (p=0) when y+z=0, and is preferably eliminated from the interior units of the siloxane chain as a result of polymerization such that p=1, p'=0, p"=1.

A preferred form of formula I where z=1 is as follows:

$$\text{Si}(XR^1)_m(R^2)_n(R^3)_o(OR^4) \atop | \atop [\text{OSi}(XR^1)_{m'}(R^2)_{n'}(R^3)_{o'}]_y \atop | \atop \text{OSi}(XR^1)_{m''}(R^2)_{n''}(R^3)_{o''}OR^4} \quad (Ia)$$

Where y+z=0, the formula becomes:

$$\text{Si}(XR^1)_m(R^2)_n(R^3)_o(OR^4)_p \quad (Ib)$$

wherein m+n+o+p is 4 or 5, normally 4, particularly:

$$\text{Si}(XR^1)_2R^2R^3 \quad (Ic),$$

or $$\text{Si}(XR^1)_3R^3 \quad (Id)$$

wherein X is preferably oxygen.

Figure 2:
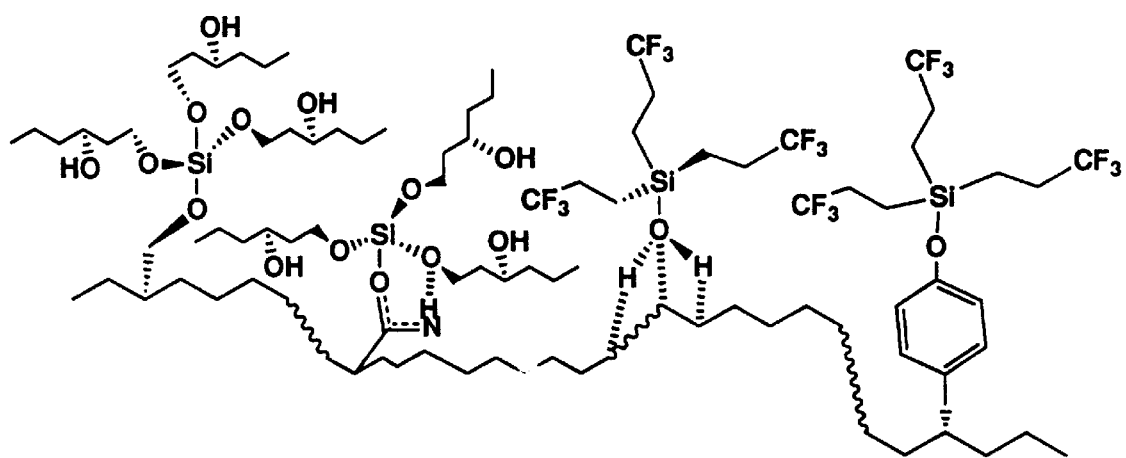

FIG. 1 represents a polysiloxane of formula Ib bound to the skin, whereas FIG. 2 depicts a number of siloxane compounds of formula Id bound to the skin. FIG. 1 shows the siloxane polymer bridging the bioactive agent and skin, wherein (a) and (b) are the strengths of the bonds between the bioagent and skin, respectively, and the siloxane. The values of (a) and (b) will determine relative substantivity versus slow release characteristics. Phenylalanine, serine, any amide group (asparagine, glutamine, backbone) and tightly protein-bound water demonstrate skin functionalities that bond the siloxane, while 1,3-hexanediol (an insect repellent), glycerol (a humectant), a trifluoropropyl group (a chemical repellent), and a polysaccharide (a humectant) demonstrate bioactive agent functionalities that bond the siloxane.

The complex of formula I can be created either by in situ ternary or binary formation. For ternary formation, a formulation of separate compounds including the silane coupling agent and the bioactive agent are mixed on the skin as represented below:

Bioactive Agent+Silane Coupling Agent+Skin

Alternatively, binary formation requires the preparation of a bioactive agent-silane coupling agent compound which is formulated in a stable composition and delivered to the skin as a bioactive-specific silane coupling agent. Binary mixing with the skin, as represented below, can result in a higher density of bioactive agent per silicon:

Bioactive Agent+Silane Coupling Agent+Skin

The molecular composition of a binary agent for creating skin-bonded siloxane complexes of formula I can be represented generically by the formula:

$$\text{Si}(XR^1)_m(R^2)_n(YR^4)_p \atop | \atop [\text{OSi}(XR^1)_{m'}(R^2)_{n'}(YR^4)_{p'}]_y \atop | \atop [\text{OSi}(XR^1)_{m''}(R^2)_{n''}(YR^4)_{p''}]_z \quad (II)$$

wherein m, n, p, m", n", and p", which may each be the same or different, are each 0, 1, 2, 3 or 4, preferably 0, 1, 2 or 3, and m', n', and p', which may each be the same or different, are each 0, 1, 2, or 3, preferably 0, 1 or 2, provided that the sum of m+n+p is from 3 to 5, preferably 3 or 4, the sum of m'+n'+p' is from 2 to 3, preferably 2, and the sum m"+n"+p" is from 3 to 4, preferably 3, and further provided that the molecule contains at least one group —XR$^1$ and at least one group R$^4$, the other substituents having the meanings defined above for formula I.

Where y+z=0, the formula becomes:

$$Si(XR^1)_m(R^2)_n(OR^4)_p \quad \text{(IIa)}$$

wherein m+n+o+p is 4 or 5, normally 4, $R^2$ is preferably $C_1$–$C_4$ alkyl and $R^4$ is preferably $C_2$–$C_4$ alkyl, particularly:

$$Si(XR^1)R^2(OR^4)_2 \quad \text{(IIb)},$$

or $$SiXR^1(OR^4)_3 \quad \text{(IIc)}$$

wherein X is most often oxygen (—O—).

For the ternary system, a pair of reagents having the formulas IIIa and IIIb are used:

$$\begin{array}{l} Si(R^2)_n(YR^4)_p \\ | \\ [OSi(R^2)_{n'}(YR^4)_{p'}]_y \\ | \\ [OSi(R^2)_{n''}(YR^4)_{p''}]_z \end{array} + \quad \text{(IIIa)}$$

$$R^1XH \quad \text{(IIIb)}$$

wherein n, p, n" and p", which may each be the same or different, are each 0, 1, 2, 3 or 4, preferably 0, 1, 2 or 3, and n', and p', which may be the same or different, are each 0, 1, 2, or 3, preferably 0, 1 or 2, provided that the sum of n+p is from 3 to 5, preferably 3 or 4, the sum of n'+p' is from 2 to 3, preferably 2, and the sum n"+p" is from 3 to 5, preferably 3 or 4, and further provided that the molecule of formula (IIIa) contains at least two, preferably at least three groups —$YR^4$, the other substituents having the meanings defined above for formula I. The coupling reaction between IIIa and IIIb results in elimination of $R^4YH$, which should be a non-toxic compound if the reaction is to occur in-situ on the skin.

The coupling group —X— between the bioactive agent and the siloxane is usually an alcohol or phenol, but can also be a sulfide, amide, carboxylate or amine of appropriate stability. While the silane coupling groups —Y— are usually the same as —X—, X and Y can be different. $R^4$ is generally any group that allows rapid hydrolysis of the Si—Y bond to form a silanol, Si—OH or Si—OM, wherein M is a cation such as Na+ or K+.

If gradual release of the bioactive agent is needed, as with an insect repellent for —$XR^1$, the bridging bond (a) in FIG. 1 between the silane and the bioactive agent must be made somewhat reversible. For this purpose, the linking portion of —x— should not be carbon, i.e., no Si—C bond should be formed. If the bioactive agent is volatile or toxic, this bond should be less reversible, preferably Si—C or Si—$OR^1$ wherein $R^1OH$ would be a secondary or tertiary alcohol, and the reaction leading to the ternary complex must occur quickly relative to the rate of evaporation or skin absorption.

For more precise timed release, a specialized silane coupling agent-bioactive agent of formula II may be synthesized such that X is appropriate for the rate of release desired. For example, secondary and tertiary alcohols will provide slower release than primary alcohols. Primary amines and sulfides will provide even more rapid release than alcohols.

Silane coupling agents of formula II and IIIa include a variety of specific compounds such as mono-, di-, tri- and tetra-alkoxy silanes, mono-, di-, tri- and tetra-amino silanes, polysilanols, and special silane coupling agents such as dissilazanes, bis(silyl)carbonates, and bis(silyl)ureas. An organic group attached directly to the silicon atom can control three functions: (1) rate of reaction, (2) general topical toxicity/cosmetic properties, and (3) skin surface or bioactive functionality. Bulky alkyl groups such as isopropyl and t-butyl slow the rate of reaction at the silicon atom, while small polar groups such as gamma-aminopropyl enhance the rate of reaction at the silicon. Alkyl or aryl radicals $R^2$ containing one to twenty carbon atoms are useful for controlling topical toxicity or cosmetic properties (look, feel, color, etc). Trifunctional coupling agents having three reactive Si bonds are most preferred; this corresponds to n=1 in formulas II and IIIa above.

A key requirement for these coupling agents is that, when the reaction on the skin surface yields the polymerized siloxane and one or more byproducts, the byproduct(s) should be safe materials preferably having useful cosmetic properties. If X and/or Y are O (oxygen) in formulas II or IIIa, then the agent is sil-oxy. If X and/or Y is —NH—, then the coupling agent is a silyl-amine. For these agents, the group $R^4$ bound to N or O is preferably an alkyl or aryl group with one to twelve carbons. For the alkoxy-silane, $R^4$ is most preferably alkyl with two to four carbon atoms, aryl with six carbon atoms, or benzyl.

For the silyl-amine, $R^4$ is preferably ethyl or —$CH_2CH_2OH$. For this agent, the H on the N could be a hydrocarbyl group instead (—NR—). However, this would lead to a secondary amine by-product, which is undesirable because of the high potential for these amines to form carcinogenic nitroso derivatives. Thus, the primary amine is preferred. A tertiary amine is possible, and preferred —$YR^4$ groups would be triethylamino or triethanolamino, but this silyl derivative will be highly unstable.

A special group of secondary amines that are useful coupling agents and yield safe by-products are represented by the silyl-imidazoles and silyl-indoles. These coupling agents occur when —$YR^4$ is an imidazole or indole radical, or a derivative thereof, preferably methyl or phenyl substituted. These nitrogen ring radicals are bound to the silicon through a nitrogen atom, and thus are somewhat like the amines.

If —$YR^4$ is OH or OM, then the coupling agent is a silanol (for OH) or silanolate (for OM). If —Y— is S instead of O, a thio-silane coupling agent results. For the thio derivatives, $R^4$ can be alkyl or aryl as for the siloxy compounds, or H or M similar to the silanol and silanolate derivatives.

If —$YR^4$ is —NR'—CO—$R^4$, then the agent is a silyl-amide. In this case R' could be H or a primary alkyl group with 1–5 carbon atoms, preferably hydrogen or methyl, and $R^4$ could be H or an alkyl or aryl group with one to twelve carbon atoms, or have structure corresponding to an amino acid or peptide derivative. For example if —$YR^4$ is $CH_3CONHCH_2$—CONH—, then the agent would be a silyl-N-acetyl-glycine-amide. The advantage of using silyl-peptide-amides is that the byproduct of the binding reaction with the skin is an amino acid or peptide, which are commonly used in cosmetic formulations. A slight modification of the silyl-amide to form a silyl-urea would also be useful as a coupling agent. A silyl-urea would result from Y being the radical —NHCONH—, such that the Si—$YR^4$ radical Si—$NHCONHCH_3$ would represent a N-methyl-N-silyl urea. A special case of this type of silyl compound would be that noted above, the bis(silyl)urea When the Si—$YR^4$ group is the radical Si—O—CO—R, the silane coupling agent is a silyl-O-ester. In this case R can be an alkyl, alkenyl or aryl group with one to twenty carbons, preferably one of the common cosmetic fatty acids such as laurate (R=C11), myristate (R=C13), palmitate (R=C15), stearate (R=C17), oleate (R=C17, 1 double bond), linoleate (R=C17, 2 double bonds), and linoleneate (R=C17, 3 double bonds), or an aryl group with six carbons, or a benzyl group. If the Si—$YR^4$ group is the radical Si—CO—

O—$R^4$, the silane coupling agent is a silyl-C-ester. $R^4$ is the same as for the silyl-O-esters described above.

A group that contains both the acid and the amide functionality would be a silyl-carbonate. In this case Y would be —NH—CO—O—, and depending on whether the Si was bonded to the N or the O, the compound would be a silyl-N-carbonate or silyl-O-carbonate, respectively. $R^4$ is as described above for the silyl-ester. For a special case of the carbonate, the bis(silyl)carbonate, the desired skin surface functionality (—$XR^1$) is incorporated as a substituent on at least one of the silicon atoms.

The selection of the silane binding agent will depend on the method of coupling to the skin and the stability of the agent in the formulation. A key requirement is that the silane coupling agent must still be substantially activated, that is, the majority of the silane must be in a reactive form (either the original form or the silanol form) at the time it is presented to the skin surface. For most applications, the silane binding agent will typically be a trifunctional-alkoxysilane, for example, of the formula $SiOR^1R^2(OR^4)_2$ or $Si(OR^1)_2R^2OR^4$. The advantages of this silane are the low toxicity of the coupling agent and its byproducts, the ability to form high molecular weight polymers on the skin, as well as the ability to react with functional groups both on the skin and in the bioactive agent to be adhered to the skin surface.

Other silane binding agents may prove optimal under certain circumstances. Tetra-functional silane binding agents lacking the $R^2$ group will not usually be useful due to the unacceptable toxicity of these compounds. However, if an agent such as sodium tetra-silanolate can be formulated to react very rapidly with the skin surface, toxicity may not be a problem.

In partially prepolymerized polysiloxanes according to the invention, reactive functionalities must be present at the time of delivery, and the size of the polymer should be limited by y being less that 5,000, preferably less than 500. Efficient coupling and overall control of release can be enhanced by preparing specialized silane coupling agents of formula II for each bioactive agent that is to be attached to the skin surface, as shown in Table 1.

TABLE 1

| Topical Agent | Silane-Agent Formula |
|---|---|
| A. Antimicrobials | |
| Phenol | |
| HO—⟨phenyl⟩ | Et—Si(OEt)(OEt)—O—⟨phenyl⟩ |
| Cresol (o, m, p) | |
| HO—⟨phenyl⟩—Me | Et—Si(OEt)(OEt)—O—⟨phenyl⟩—Me |
| Hydroxy-Benzoates | |
| HO—⟨phenyl⟩—Me | Et—Si(OEt)(OEt)—O—⟨phenyl⟩—$CO_2H$ |
| Resorcinol/4-hexylresorcinol | |
| HO—⟨phenyl(OH)⟩—($C_6H_{13}$) | Et—Si(OEt)(OEt)—O—⟨phenyl(OH)⟩—($C_6H_{13}$) |
| Hexachlorophene | |
| Cl,Cl-dihydroxy-diphenylmethane (hexachlorophene structure) | Silyl-ether of hexachlorophene with Et—Si(OEt)(OEt)—O— group |

TABLE 1-continued
| Topical Agent | Silane-Agent Formula |
|---|---|
| Triclosan 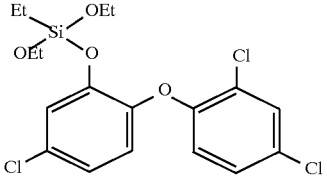 | 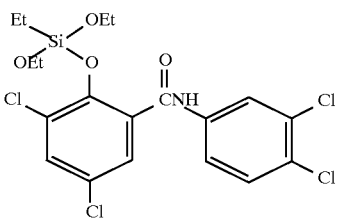 |
| Salicylanilide | |
| Tetracycline | |
| (Quinolones) | |
| Peptides and Derivatives: | |
| Bacitracin, Gramicidin, Polymyxin B | |
| Glycosidic: | |
| Streptomycin B, Neomycin A, Erythromycin, Gentamicin | |

TABLE 1-continued
| Topical Agent | Silane-Agent Formula |
|---|---|
Others:
Chlorhexidine
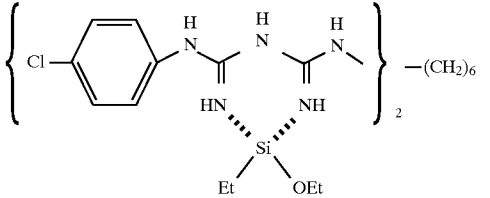
Thiols/Antidandruff pyrithione
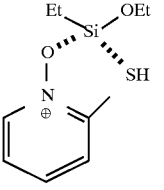
Imidazoles/Antifungals miconazole
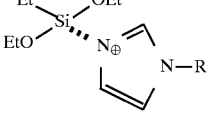
Topical Germicidals such as Acids/Surfactants
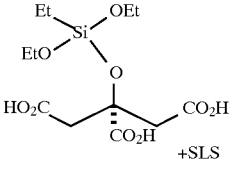
Mercurials such as thimersal
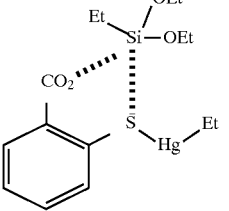
Ureas such as triclocarban, cloflucarban
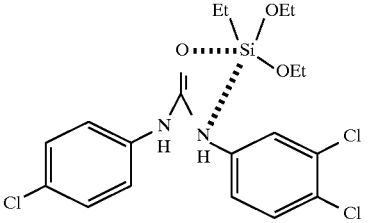

TABLE 1-continued
| Topical Agent | Silane-Agent Formula |
|---|---|
| Penicillins 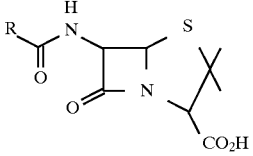 | 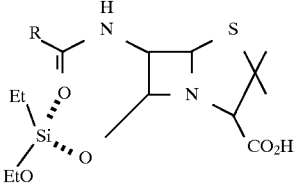 |
| Quaternary $C_{18}H_{37}-\overset{\oplus}{N}-(CH_3)_3$ $Cl_{\ominus}$ | $C_{18}H_{37}-\overset{\oplus}{N}-(CH_3)_2(CH_2)_3-Si-(OEt)_3$ $Cl_{\ominus}$ |
B. Sunscreens
| | |
|---|---|
| Benzoates 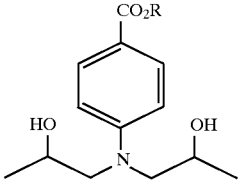 | 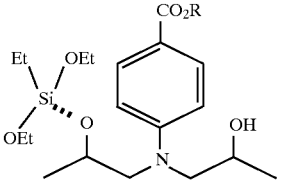 |
| Oxybenzone (dioxy) 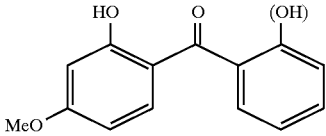 | 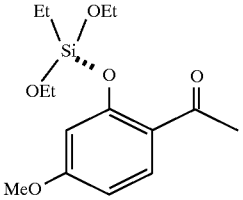 |
| Cinnamic Acid Derivatives 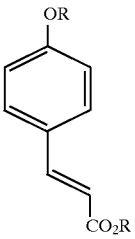 | 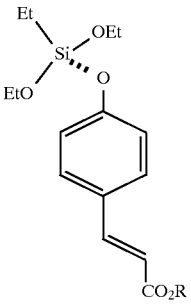 |

TABLE 1-continued

| Topical Agent | Silane-Agent Formula |
|---|---|

C. Insect Repellents 1,3-Hexanediol

[structure: HO-CH2CH2-CH(OH)-CH2CH2CH3]

[structure: Et(EtO)2Si-O-CH2CH2-CH(OH)-CH2CH2CH3]

Citronellal

[structure of citronellal with CHO group]

[structure: Et(EtO)2Si-O- attached to cyclic/open form with OH and isopropenyl group]

Toluamide

[structure: m-methylbenzene with CON(Et)2]

[structure: Et(EtO)2Si-O-aryl with CON(Et)2 and methyl substituents] or

D. Humectants/Moisturizers

Polyols such as
Glycerol,
Polyethylene glycol
Hyaluronic acid

[structure: HO-CH2-CH(OH)-CH2-OR]

[structure: Et(EtO)2Si-O-CH2-CH(OH)-CH2-OR]

E. Skin Protectants

Silicones

[structure: [-O-Si(Me)2-O-Si(Me)2-O-]n with methoxy groups]

[structure: Et(EtO)2Si-O-Si(Me)2-O-Si(Me)2-O-O-Si(OEt)2Et]

Perfluorocarbons

[structure: [-CH2-CF2-CF2-CF2-CF2-CH2-]n]

[structure: (EtO)3Si-CH2CH2R]

TABLE 1-continued
| Topical Agent | Silane-Agent Formula |
|---|---|
| Allantoin 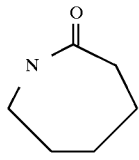 | 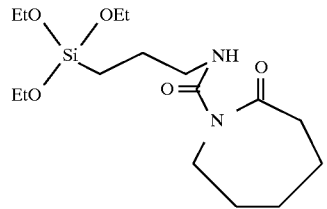 |
| Methyl Silylates 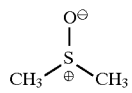 | 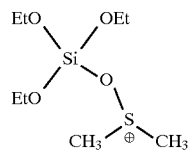 |
F. Skin Penetration Enhancers
| Caprolactams 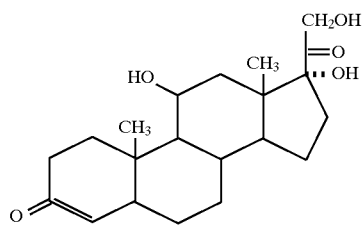 | 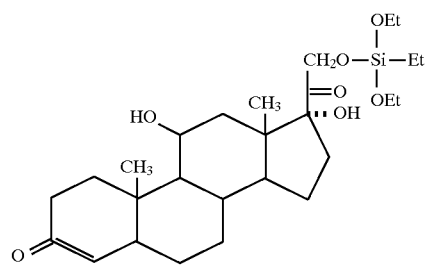 |
|---|---|
| Sulfoxides 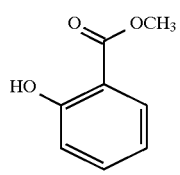 | 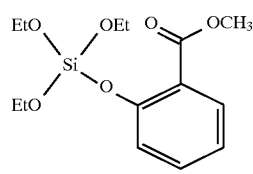 |
G. Anti-Inflammatory Agents
| Corticosteriods | |
|---|---|
| Salicylates | |

TABLE 1-continued

| Topical Agent | Silane-Agent Formula |
|---|---|
| H. Anti-Allergy Agents | |

Cromolyn

[Structure: cromolyn sodium — two chromone carboxylate units linked via O-CH2-CH(OH)-CH2-O bridge]

[Structure: silane-modified cromolyn — the central OH replaced with O-Si(OEt)3]

Pentigitide

ASP-SER-ASP-PRO-ARG

ASP—SER—ASP—PRO—ARG
|
O
|
EtO—Si—OEt
|
OEt

I. Hair Growth Agents

Minoxidil

[Structure: minoxidil with piperidine, diaminopyrimidine N-oxide]

[Structure: silane-modified minoxidil with Si(OEt)2 coordinated]

J. Skin Emollients

Alcohols            R-OH

Cetyl Alcohol
Glyceryl Hydroxystearate
PPG- and PEG- Monoesters

Et    OEt
 \\  /
  Si
 /  \\
EtO   OR

K. Antioxidants

Ascorbates

[Structure: ascorbic acid]

[Structure: silane-modified ascorbate with (EtO)2(Et)Si-O- group]

Gallates

[Structure: gallate ester — 3,4,5-trihydroxybenzoate CO2R]

[Structure: silane-modified gallate with (EtO)2(Et)Si-O- replacing one phenolic OH]

TABLE 1-continued

| Topical Agent | Silane-Agent Formula |
|---|---|

Thiocompounds

HO~S~OH

Et—Si(OEt)(OEt)—O—CH₂CH₂—S—CH₂CH₂—OH

*(silane structure: Et—Si with two OEt groups, bonded via O to ethylene-S-ethylene-OH)*

L. Hair Conditioning Agents

Proteins and Amino Acids

R-OH

Et—Si(OEt)(OEt)—R (with Et, OEt, EtO substituents on Si)

Hydroxylated Fats

Dihydroxyethyl Amine Oxide (or Glycinate)

R—N(CH₂CH₂OH)(CH₂CH₂OH) → (O or CH₂CO₂H)

R—N(CH₂CH₂OH)(CH₂CH₂O—Si(OEt)(OEt)—Et) → (O or CH₂CO₂H)

M. Coloring Agents

Phenols and Naphthols

Aminophenol
2-Naphthol
D&C Green No. 8

R-C₆H₄-OH

R-C₆H₄-O-Si(OEt)(OEt)-Et

Hydroxy azo derivatives

D&C Red No. 9
D&C Orange No. 4

*(azo-naphthol structure with HO and R substituents)*

*(silylated azo-naphthol with Et-Si(OEt)(OEt)-O- group replacing HO)*

TABLE 1-continued

| Topical Agent | Silane-Agent Formula |
|---|---|
| N. Fragrances/Flavors | |

Phenols

Menthyl Salicylate
Thymol
Vanillin

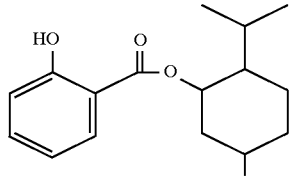 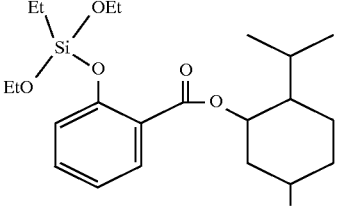

Table 1 shows the molecular formulas for preferred agents for application to skin or other body surfaces. These agents must be selected or modified to contain an appropriate bridging group between the siloxane and the biofunctional group. If the group used as a bridging group, usually alcohol or phenol, is necessary for the biological activity, then the siloxane bound derivative may not be active. This problem can be avoided by selecting a different bridging group with less specific importance for biological activity, or by utilizing a silane coupling agent that results in slow release of the active group from the siloxane. This would represent slow release where the strength of the bond between siloxane and bioactive agent is weak, as described above.

A list of the functional categories and agents for adherence to skin surfaces is set forth in J. M. Nikitakis, ed *CTFA Cosmetic Ingredient Handbook*, CTFA, 1988, and N. F. Estrin, P. A. Crosley, and C. R. Haynes *CTFA Cosmetic Ingredient Dictionary*, CTFA, 1982, the contents of which are incorporated by reference herein. See also S. S. Block, ed. *Disinfection Sterilization, and Preservation*, Lee and Febiger, 1977, for disinfectants of interest. While many of these agents will be useful unaltered because of the presence of key functional groups (alcohol, phenol, some amines, sulfhydrals, carboxylates and amides), some may need Table 1 shows the molecular formulas for preferred agents for application to skin or other body surfaces. These agents must be selected or modified to contain an appropriate bridging group between the siloxane and the biofunctional group. If the group used as a bridging group, usually alcohol or phenol, is necessary for the biological activity, then the siloxane bound derivative may not be active. This problem can be avoided by selecting a different bridging group with less specific importance for biological activity, or by utilizing a silane coupling agent that results in slow release of the active group from the siloxane. This would represent slow release where the strength of the bond between siloxane and bioactive agent is weak, as described above.

A list of the functional categories and agents for adherence to skin surfaces is set forth in J. M. Nikitakis, ed *CTFA Cosmetic Ingredient Handbook*, CTFA, 1988, and N. F. Estrin, P. A. Crosley, and C. R. Haynes *CTFA Cosmetic Ingredient Dictionary*, CTFA, 1982, the contents of which are incorporated by reference herein. See also S. S. Block, ed. *Disinfection Sterilization, and Preservation*, Lee and Febiger, 1977, for disinfectants of interest. While many of these agents will be useful unaltered because of the presence of key functional groups (alcohol, phenol, some amines, sulfhydrals, carboxylates and amides), some may need to be altered by chemical synthesis. Many of these materials can be used with success in the ternary mixing as described above, but preparing specialized silane coupling agents from each of these biofunctional agents, followed by binary mixing, may prove more efficient.

As shown in Table 1, a number of antimicrobial compounds have groups available for interaction with silanes to form siloxane coupling agents where the ethoxy group will more rapidly be hydrolyzed than the antimicrobial-siloxy bond. The disadvantage of most topically applied antimicrobial compounds is that the active ingredient is either too rapidly absorbed or too rapidly washed or wiped away, or that absorption leads to toxic side effects. For example, triclosan and trichlorocarban are relatively ineffective, probably due to rapid removal from the skin surface. Hexachlorophene is highly toxic and is rapidly absorbed by infants. Chlorhexidene is very effective, but causes severe skin drying.

Polymerizable siloxane derivatives of these compounds can maintain the agent on the skin surface for a longer time, enhancing activity and diminishing toxicity. The imino groups of chlorhexidene may be used to form bonds with the siloxane, or a phenol derivative of this popular skin germicide can be created. Creation of a long-acting germicidal surface on the skin using the organic acid and surfactant germicidal method developed for inanimate surfaces described in Belgian Patent No. 893,895 requires changing the skin pH. Successful implementation of this method in accordance with the present invention can drastically reduce transmission of disease.

Other disinfectants that carry appropriate siloxane linkage groups can also be bound to skin. Of particular interest are quaternary ammonium compounds. Dow Corning offers a polymerizable siloxane quaternary amine (product DC5700). The primary amine, gamma-aminotriethoxysilane, provides substantial microbial inhibitory activity on the skin.

Popular sunscreening agents such as aminobenzoates, benzophenones, and cinnamates are easily wiped off or absorbed. The greasy occlusive methods currently used to prolong activity of these compounds have undesirable aesthetic side effects. Attachment of these agents to the skin surface without greasy components will enhance the performance and the compliance of use of such agents in preventing skin cancer.

Insect repellents suffer similar shortcomings. Due to low molecular weight and hydrophobicity, these compounds are readily removed by absorption or evaporation. To obtain effectiveness, these products are frequently overdosed to a toxic level. Providing slow release from a skin bound siloxane can prevent such overloading. For siloxane complexes of toluamide, it may be preferable to prepare the corresponding phenol-derived compound.

Compounds applied to the skin surface to hold water (humectants and moisturizers) typically have the problem that the active component, such as glycerol, polyethylene glycol, sugar, hydrolyzed protein, or hyaluronic acid, is highly water soluble. This results in rapid removal by washing and perspiration. Attaching these materials to the skin surface by a fraction of the hydroxyl functional groups available on these compounds will enhance surface activity.

It is frequently desirable to enhance or diminish the barrier function of skin. Enhancing the barrier is useful to help prevent corrosive activities of overexposure to water, soap, ammonia, etc. Unfortunately, current skin protectant materials are easily removed by rubbing or absorption onto a material that is in contact with the skin. If such materials are bonded to the skin surface in accordance with the invention, better protection without greasy residue can be afforded. The use of trifluoropropyltriethoxysilane can help prevent chemical stains and dermatitis caused by irritants and allergens as well.

The ability to break down the barrier in one location in order to deliver pharmaceutical agents through the skin is of significant interest to the pharmaceutical industry. Typically, occlusion and organic solvents are used to achieve this goal. An alternative is to bind the organic penetrant to the stratum corneum, which performs the barrier function, using siloxane derivatives of caprolactam or DMSO according to the invention. Since the barrier function will be compromised at a location so treated for two to three weeks, a protective covering may be necessary.

The delivery of certain drugs which affect skin cells may benefit from slow release from a siloxane/skin-bound form of the drug. The target of topically applied antiinflamatory, antiallergy, and hair-growth drugs is cells near the application site. Slow release of these drugs from the epidermis can enhance delivery by preventing premature removal (rubbing off) and enhance compliance by providing more aesthetic and less frequent application. In a similar fashion, delivery of dental treatments such as fluoride (e.g., via siloxane fluorophosphate), tooth sealant, and gingivitis antimicrobials can be enhanced by providing a similar attachment to the tooth or gum surface.

Many cosmetics will perform better if attached to the epidermis. Cosmetics included in Table 1 are skin emollients, antioxidants, hair conditioners (fixers or waves), skin or hair coloring agents, and fragrances. Fragrance agents need to be reversibly bonded to the siloxane in accordance with the invention to allow slow release. Other agents that may benefit from similar delivery would include drugs such as depilatory agents, antidandruff agents, anti-acne agents, and antiaging agents (e.g., retinoic derivatives).

Skin-bonded siloxane compositions according to the invention may be made and applied by several methods. Each method involves the interaction of three essential parts, namely the skin, the silane, and the bioactive agent. The siloxane (or silane) is delivered to the skin in a form that allows safe reaction on the surface of the skin, yielding cosmetically acceptable byproducts and a siloxane, polysiloxane, or another compound according to formula I that forms a bridge between the bioactive agent and the skin surface.

The ternary method described above involves (a) initial application of the surface functional agent (e.g., sunscreen) in an appropriate vehicle directly to the skin, followed immediately by (b) applying a second component comprising the polymerizable silane in a state stable to polymerization directly to the skin. Polymerization of the siloxane, bonding of the siloxane groups to the skin, and bonding of the bioactive agent to the siloxane prepolymer occur simultaneously, the reaction typically running to completion within a few minutes. Water may be added directly to the skin or included with the bioactive agent component as a polymerization catalyst in an amount effective for that purpose. Conversely, the polymerizable silane component is preferably anhydrous to prevent premature polymerization.

In the first component, which is preferably flowable, i.e., liquid at room temperature, the bioactive agent of formula IIIb is in a concentration of 0.1–100% by weight of the vehicle. Preferred bioactive agent-containing compounds for use in this method have the structure:

$$B'—L—Z \quad (IV)$$

wherein B is the bioactive group, such as p-aminobenzoic acid (a sunscreen component), L is a linking alkylene or substituted alkylene group having 0 to 10 carbon atoms or a substituted or unsubstituted benzylene group, and Z is the reactive group making attachment to the silicon possible. Z can be selected from 13 OH (alcohol or phenol), —SH, —NH—, —NR—, —S—OH, —PH—OH, —PR—OH, Si—OH, Ti—OH, or Al—OH, and keto —(C=O)—. All components of B'—L—Z may constitute parts of an existing bioactive agent molecule, provided that attachment to the silicon does not affect activity, or if slow release is desired, that the reaction which occurs upon release (generally hydrolysis) yields the original bioactive agent. Alternatively, —L—Z may be added to an existing bioactive agent in a prior reaction where necessary to obtain the needed reactivity with the polymerizable siloxane.

The compound of formula IIIb/IV must be able to incorporate into the growing polymer on the skin surface Table 1 lists examples of formulas of bioactive agents and the corresponding siloxane modifications according to the invention. Many of these compounds were not been altered in order to obtain the needed functional groups, which were already present. For others, such as the caprolactam derivative, it is necessary to add a sidechain (linking group L) to allow addition of the siloxane functionality. General reaction schemes for performing these reactions are well known.

If flowable at the temperature for use, e.g. 5°–40° C., more commonly 20°–30° C., the first component comprising the bioactive agent of formula IIIb may be applied without a liquid vehicle. Water may be added to the first component both vehicle and catalyst. Other useful vehicles for bioactive agents include solvents listed in J. M. Nikitakis, ed *CTFA Cosmetic Ingredient Handbook*, CTFA, 1988, pages 85–86, particularly esters, SD alcohols, low molecular weight dimethyl silicones such as hexamethyl disiloxane, and cyclomethicones (tri- and tetra-siloxane).

The second component contains the polymerizable siloxane, preferably having the formula IIIa above. $R^2$ is preferably a substituted or unsubstituted $C_1$–$C_{10}$ alkyl or aryl group, especially methyl, ethyl, propyl, gammatrifluoropropyl, phenyl, or benzyl group, and $R^4$ is a substituted or unsubstituted $C_1$–$C_{10}$ alkyl or aryl group, especially ethyl, propyl, and benzyl, or a $C_1$–$C_{20}$ acyl group, especially acetyl, myristyl, palmityl, oleyl, glycyl, lysyl, or benzoyl, or a hydrogen atom (—H) or alkali metal (M). Y is preferably —O—, —NH—, —NR— or —S—, such that the type of group created in —$YR^4$ is preferably an alcohol (OH or OM), phenol, benzol, amine, amide, sulfide, ester, thioester, or sulfamide. The specific benefit of using the gamma-trifluoropropyl group for $R^2$ is to lock in the activity of the bioactive agent and create a polytetrafluoroethylene-like surface.

The second component may be a siloxane oligomer (z=1) which can be used in lieu of the monomeric form (y+z=0) provided that there are no more than about 5,000 units in the oligomer (y<5,000), preferably less than about 500 (y<500), and especially less than 10 (y+z=1 to 9). Oligomers with more than 5000 monomer units have very low reactivity to skin or bioagent groups, preventing incorporation of such groups into the polymer.

Appropriate anhydrous liquid vehicles for the polymerizable siloxane include esters, SD (standard denatured) alcohols, low molecular weight dimethyl silicones such as hexamethyl disiloxane, cyclomethicones, and any other suitable cosmetic solvent described in the above-cited references that does not permit premature polymerization of the siloxane. The concentration of the siloxane in the vehicle is about 0.5–100% by weight, preferably 25–75 wt. %, the balance being the vehicle.

The two components containing the active compounds of formulas IIIa and IIIb may be dispensed from a special delivery container that maintains separate compartments for each component and then mixes them at the moment of delivery on the skin, e.g., a dual nozzle pressurized spray container or atomizer. As a further alternative, the two components can be mixed in the same solution, providing that nothing in the solution causes premature polymerization. For example, an emulsion such as an oil-in-water or water-in-oil emulsion can be prepared that keeps the water away from the siloxane until delivery to the skin.

Alternatively, according to the binary system described above, the siloxane composition along with the bioactive agent may be applied in a single step wherein a compound of formula II comparable to the reaction product of compounds IIIa and IIIb is synthesized prior to formulation such as by a Grignard or transesterification reaction. As described above, the optimum linkage between the bioactive agent and the siloxane depends on the desired adherence to the siloxane and the skin. If X is C, then the bond is very tight and no reversibility is expected. If X is O from an unhindered primary alcohol, then some release would be expected in the presence of water. Less release can be obtained by using more hindered primary, secondary or tertiary alcohols. More release can be obtained by making X an N or S atom.

This specialized silane compound which carries both the bioactive agent and the polymerization coupling agent can be formulated with a vehicle in the same manner as described previously for the polymerizable siloxane. Several different compounds of this type may be mixed in a formulation to obtain co-oligomers or copolymers with mixed functions.

The polymerization reaction which occurs on the skin surface in accordance with the invention occurs rapidly, i.e., within 1–15 minutes after application. The reaction rate varies depending on the nature of the substituents. Where $YR^4$ is O-ethyl, the reaction is faster than for O-isopropyl, but if $YR^4$ is N(triethyl), the reaction is faster than for any OR group. The reaction is catalyzed by water, and can be further catalyzed by small amounts (ie. 0.1–1 wt. %, based on siloxane+vehicle) of amines or imidazoles (such as histidine) as polymerization catalysts added at the time of application.

In all of these delivery methods, the three components (skin, bioactive agent, and siloxane) react to yield a product as described in formula 1 and shown in FIG. 1. The only exception is the case of species shown as in FIG. 2, where polymerization does not occur because each compound of formula II or IIIa lacks sufficient groups —$YR^4$ to allow polymerization.

A preferred solution according to the invention contains from about 1–50 wt. % of the bioactive agent, in combination or prereacted with 1–50 wt. % of the polymerizable silane, effective amounts of one or more catalysts, such as 0.1–1.0 wt. % of triethylamine, gamma-aminopropyl triethoxysilane, or $Ti(OEt)_4$ together with a polydimethyl siloxane (to prevent skin drying), the balance being a solvent that prevents premature polymerization as described above.

Mixtures of bioactive compounds may also be employed in accordance with the invention, such as two different sunscreens, or a sunscreen and a coloring agent. Particularly useful combinations include: (i) sunscreen, artificial tanning color, water repellent, and skin moisturizer; (ii) skin moisturizer, skin softener, water repellent; (iii) antimicrobial, skin moisturizer, water repellent; (iv) insect repellent, skin moisturizer, water repellent; (v) poison ivy repellent, sunscreen, insect repellent; and (vi) sunscreen, insect repellent.

The present invention thus provides a skin delivery system for a wide variety of topical agents. It may be broadly applied to most topical agents which can satisfy the requirements described above, while maintaining the desired physical or biological activity. The following examples show exemplary formulations, dosages, and results.

EXAMPLE 1

Several sunscreen formulations were prepared and tested as follows. Three solutions (a), (b) and (c) were prepared:

(a) N,N-dihydroxyethyl-p-aminobenzoic acid-ethyl ester, commercially available from BASF was dissolved to a 10% (by weight) solution in a 50/50 volume mixture of ethanol/cyclomethicone.

(b) N,N-dihydroxyethyl-p-aminobenzoic acid-ethyl ester and ethyltriethoxysilane, commercially available from Petrarch were dissolved to a 10% (by weight, each) solution in a 50/50 volume mixture of ethanol/cyclomethicone.

(c) 2-hydroxypropyl-p-aminobenzoic acid-ethyl ester, commercially available from Amercol, was reacted with chlorotriethoxysilane, commercially available from SCM, in a 1:2 ratio at room temperature in absolute ethanol, using dicyclohexylamine (1:1 ratio with chlorotriethoxysilane) as the HCl scavenger. The resulting product (90% yield), N,N-di-2-triethoxysilylpropyl-p-aminobenzoic acid-ethyl ester, was dissolved to a 10% (by weight) solution in a 50/50 (by volume) mixture of ethanol/cyclomethicone.

Ten microliters of each solution (a), (b), or (c) was applied separately to a 7 $cm^2$ patch of skin, either whole nude mice or a piece of greentree python snake skin, once daily for 3 days. If solution (a) was used, then 10 $\mu l$ of ethyltriethoxysilane (ETS) was applied immediately after (a) for 5 of 10 samples. At the end of the application period, the patches were washed five times each day for three days with 20 $\mu l$ of 50/50 ethanol/water using a 3 cm diameter cylinder to enable collection of the washings. The amount of sunscreen washed off was quantified using reverse phase HPLC. The percentage remaining bound after 15 washes was designated as 100×(amount applied−amount washed off)/(amount applied) and was averaged for the 5 samples. The results are given in Table 2.

TABLE 2

| Sample/Method | Solution | % bound after: | | |
|---|---|---|---|---|
| | | 5 washes | 10 washes | 15 washes |
| Mouse control | (a) only | 7 | 4 | 4 |
| Snake control | (a) only | 5 | 1 | 1 |
| Mouse | (a) + ETS | 73 | 64 | 51 |
| Snake | (a) + ETS | 70 | 61 | 50 |
| Mouse | (b) | 81 | 73 | 60 |
| Snake | (b) | 78 | 70 | 55 |
| Mouse | (c) | 97 | 89 | 82 |
| Snake | (c) | 95 | 87 | 85 |

Additional tests using fluorescent tracers (dansyl) showed by direct measurement that sunscreen on live nude mice has a half-life of about 3 days for solution (b) and about 5 days for solution (c). Measurements using attenuated transmission Fourier transform infrared spectroscopy (AT/FTIR) of both (b) and (c) showed the presence of Si—O—Si and Si—O—C bonds. This method also showed the apparent but surprising coordination of the skin amide bonds to silicon as the amide I and II bands were split into doublets. Preliminary tests of skin erythema due to simulated sunlight exposure on guinea pigs showed a similar enhanced protection for the pigs treated with sunscreen combined with polymerizable siloxane.

EXAMPLE 2

Insect repellent formulations were prepared and tested as follows. Four solutions (a), (b), (c) and (d) were prepared:

(a) 2-Ethyl-1,3-hexanediol and ethyltriethoxysilane (ETS) were each dissolved in an amount of 10% by weight in a 50/50 mixture of ethanol/cyclomethicone.

(b) N,N-diethyl-m-toluamide and ethyltriethoxysilane were each dissolved in an amount of 10% by weight in a 50/50 mixture of ethanol/cyclomethicone.

(c) m-Toluylchloride was mixed with diethoxyamine and dicyclohexylamine in a ratio of 1:1:1 and refluxed for 24 hours in tetrahydrofuran. The product, N,N-diethoxy-m-toluamide, was obtained in a 30% yield, and the product and ethyltriethoxysilane were each dissolved in an amount of 10% by weight in a 50/50 mixture of ethanol/cyclomethicone.

(d) 2-Ethyl-1,3-hexanediol was mixed with chlorotriethoxysilane and dicyclohexylamine in a 1:1:1 ratio at 0° C. in absolute ethanol. The resulting product, 2-ethyl-1-triethoxysiloxy-3-hexanol, was obtained in 50% yield and was dissolved to a 10% by weight solution in a 50/50 by volume mixture of ethanol/cyclomethicone.

Ten microliters of each of (a), (b), (c), (d), 2-ethyl-1,3-hexanediol (EHD), N,N-diethyl-m-toluamide (DT), or N,N-diethoxy-m-toluamide (DOT) were applied to separate 7 cm$^2$ patches of greentree python snake skin once daily for 3 days. At the end of the application period, the patches were washed five times each day for three days with 20 µl of 50/50 ethanol/water using a 3 cm diameter cylinder to enable collection of the washings. The amount of insect repellent washed off was quantified using reverse phase HPLC, C$^{14}$ radiocounting or AT/FTIR. The percentage remaining bound after 5, 10, and 15 washes was designated as 100×(amount applied−amount washed off)/(amount applied) and was averaged for 5 samples. The results are given in Table 3.

TABLE 3

| Sample/Method | Solution | % bound after: | | |
|---|---|---|---|---|
| | | 5 washes | 10 washes | 15 washes |
| Snake control | EHD | 7 | 2 | 2 |
| Snake | (a) | 71 | 55 | 31 |
| Snake control | DT | 10 | 5 | 2 |
| Snake | (b) | 25 | 12 | 5 |
| Snake control | DOT | 6 | 1 | 1 |
| Snake | (c) | 73 | 60 | 45 |
| Snake | (d) | 83 | 70 | 55 |

These data suggest that the combination of a siloxane agent with an insect repellent enhances adherence of the repellent to the skin, and preparing a special silane binding agent of the repellent further enhances the skin adherence. The effect that these silane agents has on insect repellency is unknown. However, the results suggest that insect repellent can be released in a slow release fashion from the skin.

EXAMPLE 3

Humectant formulations were prepared and tested as follows. Three solutions (a), (b) and (c) were first prepared:

(a) Glycerol and ethyltriethoxysilane (ETS) were each dissolved in an amount of 10% by weight in a 50/50 mixture of ethanol/cyclomethicone.

(b) Hyaluronic acid (HA) was dissolved to 2% by weight in purified water.

(c) Glycerol (GL) was reacted with chlorotriethoxysilane (CTS) in a 1:1 ratio at 0° C. in a 50/50 mixture of ethanol/cyclomethicone, using a 1:1 ratio of dicyclohexylamine to chlorosilane as the HCl scavenger. The resulting product, 1-triethoxysilylglycerol, was obtained in 90% yield and was dissolved to a 10% by weight solution in a 50/50 by volume mixture of ethanol/cyclomethicone.

Ten microliters of (a), (b), (c), (GL), or (HA) were applied separately to 7 cm$^2$ patches of greentree python snake skin once daily for 3 days. In the case of (b), 10 µl of ETS was also applied immediately after solution (b). At the end of the application period, the patches were washed five times each day for three days with 20 µl of 10/90 ethanol/water using a 3 cm diameter cylinder to enable collection of the washings. The amount of humectant washed off was quantified using reverse phase HPLC, C$^{14}$ radiocounting or AT/FTIR. The percentage remaining bound after 5, 10, and 15 washes was designated as 100×(amount applied−amount washed off)/(amount applied) and was averaged for the 5 samples. The results are set forth in Table 4.

TABLE 4

| Sample/Method | Solution | % bound after: | | |
|---|---|---|---|---|
| | | 5 washes | 10 washes | 15 washes |
| Snake control | GL | 1 | 0 | 0 |
| Snake | (a) | 55 | 35 | 25 |
| Snake control | HA | 5 | 1 | 0 |
| Snake | (b) + ETS | 65 | 44 | 31 |
| Snake | (c) | 71 | 55 | 41 |

The results illustrate that the siloxanes applied according to the invention improved skin retention of the humectant, with the specially prepared silane-humectant showing the greatest improvement.

EXAMPLE 4

Skin smoothness formulations were prepared as follows, starting with solutions (a) and (b):

(a) Polydimethylsiloxane-ethylene glycol copolymer (PSGC) and ethyltriethoxysilane were each dissolved in an amount of 10% by weight in a 50/50 mixture of ethanol/cyclomethicone.

(b) PSGC was reacted with chlorotriethoxysilane (CTS) in a 1:1 ratio at 0° C. in a 50/50 mixture of tetrahydrofuran/cyclomethicone, using a 1:1 ratio of dicyclohexylamine to chlorosilane as the HCl scavenger. The resulting product, triethoxysilyl-PSGC, was purified by distilling off the solvent, and was dissolved to a 10% by weight solution in a 50/50 by volume mixture of ethanol/cyclomethicone.

Ten microliters of (a), (b) or PSGC were applied separately to a 7 cm² patch of greentree python snake skin once daily for 3 days. At the end of the application period, the patches were be washed five times each day for three days with 20 µl of 50/50 ethanol/water using a 3 cm diameter cylinder to enable collection of the washings. The amount of PSGC washed off was quantified using reverse phase HPLC, $C^{14}$ radiocounting or AT/FTIR. The percentage remaining bound after 5, 10, and 15 washes was designated as 10× (amount applied−amount washed off)/(amount applied) and was averaged for the 5 samples.

TABLE 5

| | | % bound after: | | |
|---|---|---|---|---|
| Sample/Method | Solution | 5 washes | 10 washes | 15 washes |
| Snake control | PSGC | 15 (2.5) | 7 (5.1) | 2 (6.5) |
| Snake control | (a) | 46 (1.5) | 31 (1.9) | 27 (2.1) |
| Snake control | (b) | 65 (1.1) | 47 (1.5) | 38 (1.2) |

The results show that siloxanes applied according to the invention improve the skin retention of skin emollients. The skin smoothness is represented by lowered skin friction (in dynes/cm²) which is maintained longer by application of the polymerizable siloxane in combination with PSGC.

EXAMPLE 5

Antimicrobial and germicidal formulations were prepared and tested as follows. The following solutions were first prepared:

(a) Aminopropyltriethoxysilane was dissolved to 10% by weight in a 50/50 mixture of ethanol/cyclomethicone.

(b) Pyrithione (PYR) and ethyltriethoxysilane were each dissolved to 10% by weight in a 50/50 mixture of ethanol/cyclomethicone.

(c) Hexachlorophene (HCP) was reacted with chlorotriethoxysilane in a 1:1 ratio at 0° C. in tetrahydrofuran, using a 1:1 ratio with chlorosilane of dicyclohexylamine as the HCl scavenger. The resulting product, hexachlorophene-mono(triethoxy)siloxy ester, was obtained in a 50% yield and dissolved in an amount of 10% by weight in a 50/50 by volume mixture of ethanol/cyclomethicone.

(d) Malic acid (MA) was mixed in a 1:1 ratio with tetraethoxysilane in tetrahydrofuran and refluxed for 24 hours. The product, ethyltriethoxysiloxymalic acid, was purified by distilling off the solvent, and dissolved to 10% by weight in a 50/50 by volume mixture of ethanol/cyclomethicone.

Ten microliters of (a), (b), (c), (d), PYR, HCP, MA, or ethyl/cyclomethicone vehicle were applied separately to a 7 cm² patch of greentree python snake skin once daily for 3 days. At the end of the application period, one-half of the patches were washed five times each day for three days with 20 µl of 50/50 ethanol/water using a 3 cm diameter cylinder to enable collection of the washings.

The patches of snake skin were assayed for antimicrobial activity using 3 methods: (1) zone of antimicrobial activity on agar due to diffusion, (2) quantitation of microbial growth in solution mixing with patch, and (3) quantitation of microbial growth on human skin. The first method was a standard zone of inhibition study in which the bacteria was streaked onto an agar plate, the disk containing the test material was placed on the plate, and then the bacteria were allowed to grow for 24 hours. The distance in millimeters that the bacteria did not grow from the edge of the disk, i.e. the bacteria free zone surrounding the disk, was measured (Table 6).

In the second test, tubes containing liquid growth medium were inoculated with bacteria, and then the test disk was placed in the tube. The bacteria was allowed to grow for 24 hours and then the number of bacteria per ml was quantified either by light reflectance or by removing a small volume and streaking on an agar plate. The latter method was followed by allowing the bacteria to grow and then counting the colonies (Table 7).

The third test involved growing normal skin bacteria by covering the skin with an occlusive dressing such as Saran Wrap (this is referred to as expanding the flora). Prior to expanding the flora, the skin test sites were treated with the test or control solutions as described above. The flora was then expanded for 24 hours, followed by quantitating the bacteria growth. This was done by washing an area of skin with liquid growth medium and spreading the washing on an agar plate. After the bacteria grew the number colonies were counted (Table 8).

In each case several microbes were tested with comparable results, but only the results for *S. aureus* are reported. Each result was averaged for samples.

TABLE 6

| | | Zone of Inhibition (mm) after: | | |
|---|---|---|---|---|
| Sample/Method | Solution | 0 washes | 5 washes | 15 washes |
| Snake control | vehicle | 1 | 0 | 0 |
| Snake compar | PYR | 10 | 0 | 0 |
| Snake compar | HCP | 18 | 0 | 0 |
| Snake compar | MA | 15 | 0 | 0 |
| Snake invention | (a) | 5 | 3 | 2 |
| Snake invention | (b) | 7 | 7 | 3 |
| Snake invention | (c) | 10 | 8 | 3 |
| Snake invention | (d) | 5 | 2 | 2 |

These results show that the antimicrobial agent leaches (is released) only a little after initial attachment, and almost not at all after washing, suggesting that the siloxanes have enhanced retention of the active compound on the skin.

TABLE 7

| | | Microbe Growth/Solution (CFU) after: | | |
|---|---|---|---|---|
| Sample/Method | Solution | 0 washes | 5 washes | 15 washes |
| Snake control | vehicle | $10^3$ | $10^3$ | $10^3$ |
| Snake comparison | PYR | 0 | $10^2$ | $10^3$ |

TABLE 7-continued

| Sample/Method | Solution | Microbe Growth/Solution (CFU) after: | | |
|---|---|---|---|---|
| | | 0 washes | 5 washes | 15 washes |
| Snake comparison | HCP | 0 | 10 | $10^3$ |
| Snake comparison | MA | 0 | $10^2$ | $10^3$ |
| Snake invention | (a) | $10^2$ | $10^3$ | $10^3$ |
| Snake invention | (b) | 0 | 10 | $10^3$ |
| Snake invention | (c) | 0 | 0 | 10 |
| Snake invention | (d) | 0 | 10 | $10^3$ |

This data shows that (a) is not microbiocidal, and (b)–(d) are microbiocidal. Activity for (b)–(d) was extended after washing due to the enhanced skin retention that the siloxanes provide when applied in accordance with this invention.

TABLE 8

| Sample/Method | Solution | Microbe Growth/on Skin (CFU) after: | | |
|---|---|---|---|---|
| | | 0 washes | 5 washes | 15 washes |
| Human control | vehicle | $10^5$ | $10^5$ | $10^5$ |
| Human compar. | PYR | 10 | $10^4$ | $10^5$ |
| Human compar. | HCP | 0 | $10^2$ | $10^5$ |
| Human compar. | MA | 10 | $10^5$ | $10^5$ |
| Human invention | (a) | 0 | $10^2$ | $10^3$ |
| Human invention | (b) | 0 | $10^2$ | $10^3$ |
| Human invention | (c) | 0 | 0 | 10 |
| Human invention | (d) | 0 | $10^2$ | $10^3$ |

These data show that the aminofunctional silane coupling agent has an inhibitory activity on bacterial growth on human skin even though previous studies showed that it was not bactericidal. This agent may block binding of bacteria to the skin, which is thought to be necessary for bacterial expansion. These results also show that, when the siloxanes are used as described in this invention, the antibacterial activity of the bactericidal compounds is enhanced on the skin surface due to the enhanced skin retention.

EXAMPLE 6

Skin protectant formulations were prepared and tested as follows using solutions:

(a) gamma-Trifluoropropyltrimethoxysilane was refluxed in absolute ethanol for 24 hours, and the solvent was distilling. The product, gamma-trifluoropropyltriethoxysilane, was dissolved to 10% by weight in a 50/50 mixture of ethanol/cyclomethicone.

(b) gamma-Aminopropyltriethoxysilane and ethyltriethoxysilane were each dissolved to 10% by weight in a 50/50 mixture of ethanol/cyclomethicone.

(c) Allantoin was dissolved to 10% by weight in a 50/50 by volume)mixture of ethanol/cyclomethicone.

(d) Allantoin (AL) was reacted with chlorotriethoxysilane in a 1:1 ratio at room temperature in a 50/50 by volume mixture of ethanol/tetrahydrofuran, using a 1:1 ratio with chlorosilane of dicyclohexylamine as the HCl scavenger. The resulting product, allantion-mono (triethoxy)siloxy ester, was purified by removing solvent, and then dissolved in an amount of 10% by weight in a 50/50 by volume mixture of ethanol/cyclomethicone.

Ten microliters (a), (b), (c), (d), AT or ethanol/cyclomethicone vehicle was applied separately to a 7 cm² patch of greentree python snake skin once daily for 3 days or to a 7 cm² patch of shaved rabbit skin. At the end of the application period, the patches were washed five times each day for three days with 20 µl of 50/50 ethanol/water using a 3 cm diameter cylinder to enable collection of the washings. The amount of skin protectant washed off was quantitated using reverse phase HPLC, $C^{14}$ radiocounting or AT/FTIR. The percentage remaining bound after 5, 10, and 15 washes was designated as 100×(amount applied−amount washed off)/(amount applied) and was averaged for the 5 samples.

The skin test on rabbits was essentially a modified Draise test for skin in which unabraded skin was studied on partially occluded sites. The skin irritation study was started following skin treatment by one of the test compounds above. In this test, after the compound was applied to the skin, a known skin irritant, 10 µl of 5% salicylic acid in a 50/50 by volume mixture of ethanol/water, was applied once a day for 3 days. The skin was rated for erythema using the scale of 0-no erythema to 4-severe erythema.

TABLE 9

| Sample/Method | Solution | % bound after: | | |
|---|---|---|---|---|
| | | 5 washes | 10 washes | 15 washes |
| Snake | (a) | 81 | 75 | 68 |
| Snake | (b) | 76 | 65 | 48 |
| Snake AL control | (c) | 10 | 0 | 0 |
| Snake | (d) | 47 | 36 | 21 |

These results show that these specialized siloxanes (trifluoro-functional and amino-functional) provide wash-resistant adherence to skin when applied as described by this invention. The results also show that the skin retention of skin protectant allantoin is enhanced when applied with a polymerizing siloxane as described by this invention.

TABLE 10

| Sample/Method | Solution | Erythema Score (Draise 0–4) after: | | |
|---|---|---|---|---|
| | | 0 washes | 5 washes | 15 washes |
| Rabbit control | vehicle | 2 | 3 | 4 |
| Rabbit | (a) | 0 | 1 | 2 |
| Rabbit | (b) | 0 | 1 | 3 |
| Rabbit AL control | (c) | 1 | 3 | 4 |
| Rabbit | (d) | 0 | 2 | 3 |

These results show that while allantion does provide some protection from skin erythema by salicylic acid, this protection is lost if the skin is washed. This also shows that when polymerizable siloxanes are used in accordance with the invention, the skin retains protection from erythema.

EXAMPLE 7

Skin anti-inflammatory formulations are prepared as the following solutions:

(a) Hydrocortisone and ethyltriethoxysilane are each dissolved to 10% by weight in a 50/50 mixture of ethanol/cyclomethicone.

(b) Hydrocortisone is reacted with chlorotriethoxysilane in a 1:1 ratio at room temperature in tetrahydrofuran, using a 1:1 ratio with chlorosilane of dicyclohexylamine as the HCl scavenger. The resulting product, hydrocortisone-mono(triethoxy)siloxy ester, is purified by removing solvent, and then dissolved in an amount of 10% by weight in a 50/50 by volume mixture of ethanol/cyclomethicone.

EXAMPLE 8

Skin anti-allergy formulations are prepared as the following solutions:

(a) Cromolyn and ethyltriethoxysilane are each dissolved to 10% by weight in a 50/50 mixture of ethanol/cyclomethicone.

(b) Cromolyn is reacted with chlorotriethoxysilane in a 1:1 ratio at room temperature in tetrahydrofuran, using a 1:1 ratio with chlorosilane of dicyclohexylamine as the HCl scavenger. The resulting product, cromolyn-triethoxysiloxy ester, is purified by removing solvent, and then dissolved in an amount of 10% by weight in a 50/50 by volume mixture of ethanol/cyclomethicone.

EXAMPLE 9

Skin penetration formulations are prepared as follows:

(a) Dimethylsulfoxide (DMSO) and ethyltriethoxysilane are each dissolved to 10% by weight in a 50/50 mixture of ethanol/cyclomethicone.

(b) DMSO is reacted with chlorotriethoxysilane in a 1:1 ratio at room temperature in tetrahydrofuran, using a 1:1 ratio with chlorosilane of dicyclohexylamine as the HCl scavenger. The resulting product, dimethylsulfoxidetriethoxysiloxy ester, is purified by removing solvent, and then dissolved in an amount of 10% by weight in a 50/50 by volume mixture of ethanol/cyclomethicone.

EXAMPLE 10

Hair conditioner formulations are prepared as follows:

(a) Hydrolyzed protein and ethyltriethoxy-silane are mixed to 10% and 2%, respectively, by weight in a 50/50 mixture of water/ethanol.

(b) Dihydroxyethyl cocamineoxide (DHC) is reacted with chlorotriethoxysilane in a 1:1 ratio at room temperature in tetrahydrofuran, using a 1:1 ratio with chlorosilane of dicyclohexylamine as the HCl scavenger. The resulting product, DHC-triethoxysiloxy ester, is purified by removing solvent, and then dissolved in an amount of 10% by weight in a 50/50 by volume mixture of ethanol/cyclomethicone.

EXAMPLE 11

Antipsoriasis and antiacne formulations are prepared as follows:

(a) Salicylic acid and ethyltriethoxysilane are mixed to 10% by weight in a 50/50 mixture of ethanol/cyclomethicone.

(b) Anthralin is reacted with chlorotriethoxysilane in a 1:1 ratio at room temperature in tetrahydrofuran, using a 1:1 ratio with chlorosilane of dicyclohexylamine as the HCl scavenger. The resulting product, anthralin-triethoxysiloxy ester, is purified by removing solvent, and then dissolved in an amount of 10% by weight in a 50/50 by volume mixture of ethanol/cyclomethicone.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

I claim:

1. A siloxane compound of the formula:

(II)

wherein —$XR^1$ represents a bioactive agent selected from sunscreens, antimicrobials, deodorants, skin protectants, chemical repellents, skin moisturizers, insect repellents, skin colorants, and topical pharmaceuticals attached to the silicon atom; $R^2$ represents a $C_1$–$C_{20}$ substituted or unsubstituted alkyl, aryl or aralkyl group that reduces toxicity and improves aesthetic/cosmetic properties including viscosity and feel; $R^4$ represents unreacted coupling groups selected from H or a $C_1$–$C_{20}$ substituted or unsubstituted alkyl, aryl or aralkyl group, or a monovalent metal M such as sodium or potassium; X is a linking group of the formula —NR—, —$CR_2$—, —O—, —S—, or —P—, wherein R is hydrogen or lower substituted or unsubstituted alkyl, and an N, C, O, S or P atom is directly bonded to the Si atom; Y is a linking group of the formula —NH—, —NR—, —$CH_2$—, —CHR—, —$CR_2$—, —O—, —S—, —PH—, —PR—, —O—CO—, —NH—CO—NH—, —NR—CO—O—, —NR—CO— or —NH—CO—, wherein an N, O, S or P atom is directly bonded to the Si atom; y is from 0 to about 1 million, z is 0 or 1, provided that if z=0 then y=0; m, n, p, m", n", and p", which may each be the same or different, are each 0, 1, 2, 3 or 4, and m', n', and p', which may each be the same or different, are each 0, 1, 2, or 3, provided that the sum of m+n+p is from 3 to 5, the sum of m'+n'+p' is from 2 to 3, and the sum m"+n"+p" is from 3 to 4, and further provided that:

(1) the molecule contains at least one group —$XR^1$; and at least one group —$R^4$;

(2) the molecule contains at least one group —$XR^1$ for approximately each 200 silicon atoms.

2. The siloxane compound of claim 1, wherein the compound has the formula:

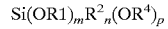

or an oligomer or polymer thereof, wherein m is 1, 2, or 3, n is 0, 1 or 2, p is 1, 2 or 3, the sum of m+n+p being 4.

3. The siloxane compound of claim 2, wherein $R^1$ represents a sunscreen group, $R^2$ is $C_1$–$C_4$ alkyl and $R^4$ is $C_2$–$C_4$ alkyl, an alcohol of the formula $R^1OH$ is other than an unhindered primary alcohol, and the sunscreen group includes a benzene ring.

4. The siloxane compound of claim 3, wherein the oxysilane has the formula $SiOR^1(OR^4)_3$.

5. The siloxane compound of claim 3, wherein the oxysilane has the formula $Si(OR^1)R^2(OR^4)_2$.

6. The siloxane compound of claim 3, wherein $R^1$ is a cinnamic acid derivative.

7. The siloxane compound of claim 3, wherein $R^1$ is a benzoate.

8. The siloxane compound of claim 3, wherein $R^1$ is a oxybenzone.

9. A siloxane-skin-bioactive agent complex having the formula:

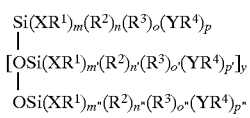

(I)

wherein —XR¹ represents the bioactive agent attached to the silicon atom; R² represents a group that reduces toxicity and improves aesthetic/cosmetic properties including viscosity and feel; R³ is a skin surface group; R⁴ represents unreacted coupling groups which react to form a siloxane polymer or oligomer, react with the skin, or react with compounds of the formula R¹XH; X is a linking group wherein an N, C, O, S or P atom is directly bonded to the Si atom; Y is a linking group wherein an N, O, S or P atom is directly bonded to the Si atom; y is from 0 to about 1 million; m, n, o, p, m', n', o', p', m", n", o" and p", which may each be the same or different, are each 0, 1, 2, 3 or 4, provided that the sum of m+n+o+p is from 3 to 5, the sum of m'+n'+o'+p' for each Si atom is from 2 to 3, and the sum m"+n"+o"+p" is from 3 to 4, and further provided that:

(1) the molecule contains at least one group —XR¹ and at least one group R³;

(2) the molecule contains at least one group R³ for approximately each 1,000 silicon atoms; and (3) the molecule contains at least one group —XR¹ for approximately each 200 silicon atoms.

10. The complex of claim 9, wherein —XR¹ is selected from a sunscreen, skin moisturizer, an antimicrobial agent, skin protectant, skin penetration enhancer, and coloring agent, and X is a linking group other than one forming an Si—C bond or —O— wherein R¹XH is a primary alcohol.

11. The complex of claim 9, wherein R² is substituted or unsubstituted C₁–C₂₀ alkyl, aryl or aralkyl group, and R⁴ is H, a substituted or unsubstituted C₁–C₂₀ alkyl, aryl or aralkyl group, or a monovalent metal M selected from sodium and potassium; X is —NR—, —CR₂—, —O—, —S—, or —P—, wherein R is hydrogen or lower substituted or unsubstituted alkyl; and Y is —NH—, —NR—, —CH₂—, —CHR—, —CR₂—, —O—, —S—, —PH—, —PR—, —O—CO—, —NH—CO—NH—, —NR—CO—O—, —NR—CO— or —NH—CO—.

12. The compound of claim 1, wherein —XR¹ is an antimicrobial agent.

13. The compound of claim 12, wherein X is a linking group other than one forming an Si—C bond or —O— wherein R¹XH is a primary alcohol.

14. The compound of claim 13, wherein the antimicrobial agent is selected for the group consisting of phenol, cresols (o,m,p), hydroxybenzoates, resorcinol, 4-hexylresorcinol, hexachlorophene, triclosan, salicylanilide, tetracycline, quinolones, bacitracin, gramicidin, polymyxin B, streptomycin B, neomycin A, erythromycin, gentamicin, chlorhexidine pyrithione, miconazole, thimersal, triclocarban, cloflucarban, and penicillins.

15. The compound of claim 13, wherein the antimicrobial agent is a chlorhexidine.

16. The compound of claim 13, wherein the antimicrobial agent is a salicylanilide.

17. The compound of claim 13, wherein the antimicrobial agent is a hexachlorophene.

18. The complex of claim 10, wherein —XR¹ is an antimicrobial agent.

19. The complex of claim 18, wherein the antimicrobial agent is a chlorhexidine.

20. The compound of claim 15, wherein the compound has the formula Si(NR¹)₂R²(OR⁴), wherein R¹ is a chlorhexidene group.

21. The compound of claim 20, wherein R² and R⁴ are ethyl groups.

22. The compound of claim 21, having the formula:

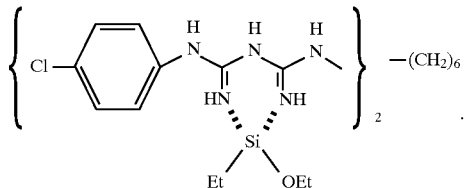

* * * * *